United States Patent [19]

Subramanyam et al.

[11] Patent Number: 5,620,951
[45] Date of Patent: Apr. 15, 1997

[54] ETHOXYLATED ALKYL GLYCEROL ETHER SULFONATES CONTAINING COMPOSITIONS

[75] Inventors: Ravi Subramanyam, North Brunswick; Ben Gu, East Brunswick, both of N.J.

[73] Assignee: Colgate-Palmolive Company, New York, N.Y.

[21] Appl. No.: 411,358

[22] Filed: Mar. 27, 1995

Related U.S. Application Data

[63] Continuation-in-part of Ser. No. 373,140, Jan. 17, 1995, abandoned.

[51] Int. Cl.$^6$ .................... C11D 3/12; C11D 1/18; C11D 9/30
[52] U.S. Cl. .................. 510/153; 510/141; 510/152; 510/156
[58] Field of Search .................... 252/549, 554, 252/546, 544, 117, 121; 562/30, 108, 110, 111

[56] References Cited

U.S. PATENT DOCUMENTS 5,310,508  5/1994  Subramanyam et al. ............... 252/549

*Primary Examiner*—Paul Lieberman
*Assistant Examiner*—Necholus Ogden
*Attorney, Agent, or Firm*—Martin B. Barancik

[57] ABSTRACT

A composition comprising an ethoxylated alkyl glyceryl ether sulfonate wherein the alkyl is twelve to fifteen carbon atoms, with no more than about 50 wt. % branched alkyl, no more than about 20 wt. % alkenyl, the average number of ethoxy groups is one, and no more than about 25 wt. % of the sulfonate components having ethoxy groups with a value of four or more.

4 Claims, No Drawings

ETHOXYLATED ALKYL GLYCEROL ETHER SULFONATES CONTAINING COMPOSITIONS

This application is a continuation-in-part of Ser. No. 8/373,140, filed on Jan. 17, 1995, now abandoned.

BACKGROUND OF THE INVENTION

U.S. Pat. No. 5,310,508 (508) discloses ethoxylated alkyl glyceryl ether sulfonates for use in personal care compositions. Particularly useful molecules were those having alkyl groups of twelve to fifteen carbon atoms, inclusive and those molecules with an average number of ethoxies of 1, 2 or 3, "n number", most specifically an average value of n equal to 1. In 508, incorporated by reference herein, the general distribution of an ethoxylated alkyl glyceryl ether sulfonate with an average value of n is 1 is provided showing the various quantity of components having n as a value of zero, 1, 2, 3, 4, 5, 6 etc. There is no indication of the members of the distribution effect on activity, mildness, lathering, ease of preparation or any other function.

It has now been discovered that the quantity of the particular number of ethoxy groups has a marked effect in the value of ethoxylated alkyl glyceryl ether sulfonates as a surfactant. The particular distribution of the ethoxylated moieties making up a value equal to average value of 1 or 2, preferably 1, should maximize the value of n is one or 2 while minimizing the quantity of any material with an n value of over three. The component where n is zero remains a significant contributor to the performance of the overall composition since a low average n value, one or two preferably one, generally requires a significant amount of n is zero component. However, the negative contribution of the higher ethoxylated moieties, n greater than three, was unexpected and not predictable. Still further, the alkyl group is preferably straight chain as opposed to branched. The average number of ethoxy groups as well as the number of ethoxyl groups having a value of four or more can have a clear bearing on lathering, as well as on the processability of the material into a shaped solid composition useful for personal care, such as a bar. This is particularly accentuated when a free fatty acid is also present. While using ordinary bar making equipment even ethoxy alkyl glyceryl ether sulfonates with an average value of 2 ethoxy groups encountered substantial difficulty being made into bars because of the inability to shape and/or release the bar at an acceptable rate from ordinary manufacturing equipment.

SUMMARY OF THE INVENTION

In accordance with the invention, there is a composition comprising an ethoxylated alkyl glyceryl ether sulfonate wherein the alkyl is twelve to fifteen carbon atoms with no more than about 50% of the alkyl group having a branch therein and no more than about 20 wt. % alkenyl, the average value of ethoxy is one, no more than about 25 wt. % of the sulfonate components have ethoxy groups with a value of four or more. The counterion can be sodium, potassium, ammonium or substituted ammonium catons, preferably alkanol (triethanolamine). The counterion is preferably sodium.

A further aspect of the invention is a personal cleansing composition of the above composition, particularly where the cleansing composition is in a shaped solid form, for example a bar.

A still further aspect of the invention is a shaped solid personal cleansing composition wherein there is about 3 to about 9 wt % preferably, about 4 to about 8 wt. % of ethoxy alkyl glyceryl ether sulfonate, with an average value of one ethoxy, about 2 to about 8 wt. % of free fatty acid, preferably no more than about 7 wt. % and a range of moisture of from about 4 to about 13 wt. % moisture, preferably about 5 or 6 to about 10 wt. % moisture. It is preferable to have a significant quantity of soap present in these compositions. With respect to the ethoxy alkyl glyceryl ether sulfonates of this paragraph, the alkyl is from about ten to twenty carbonatoms in length. Preferably the alkyl is at least about 50 wt. % normal. Preferably the average value of ethoxy is about one and preferably no more than about 25 wt. % of the sulfonate components have ethoxy groups with a value of four or more.

DETAILED DESCRIPTION OF THE INVENTION

The ethoxylated alkyl glyceryl ether sulfonates of the invention have as their major constituent the component

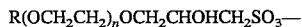

Wherein R is alkyl, about 10 to about 20 carbon atoms, preferably alkyl of about 12 to about 15 carbon atoms, preferably normal, and n is an average value one or two, preferably one.

Other materials present in lesser quantity are what is generally known as the dimer and the trimer, as depicted below wherein R and n are as previously defined.

Dimer

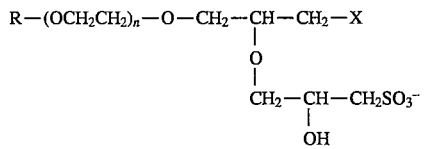

Trimer

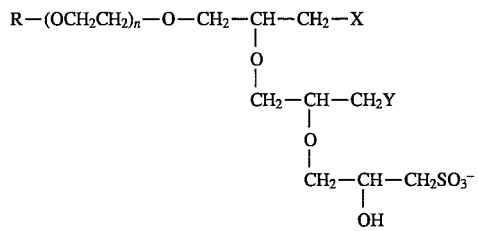

X and Y are the same or different and are selected from the group consisting of hydroxy, chloro or sulfonate anion.

The most effective surfactant properties coupled with an excellent mildness can occur with a composition wherein the alkyl is twelve to fifteen carbon atoms in length, and is substantially normal, that is no more than about 50 wt. % branched that is at least about 50 wt. % normal alkyl, preferably no more than about 30 wt. % branched and more preferably no more than about 20 wt. % branched and there is no more than about 20 wt. % alkenyl groups therein that is to say no more than about 20 wt % of the alkyl group have unsaturation present, a common presence when the alkyl group is derived from a natural product product such as coconut oil. Preferably no more than about 10 wt. %, and even more preferably no more than about 5 wt. % alkenyl is present. These chain lengths bring about an excellent balance of properties between surfactant activity and mildness. The compositions are significantly milder than the nonethoxylated material alkyl glyceryl ether sulfonate sometimes referred to as AGES or AGS.

Of particular interest is the composition wherein the average value of the ethoxy group is one, that is monoethoxy. When an average value of ethoxy equal to two is employed, the composition is essentially unprocessable into a shaped solid personal cleansing composition, particularly where a free fatty acid is present. For example, experiments with an ethoxy alkyl glyceryl ether sulfonate composition having an average ethoxy content of 2 (actual was 2.25, rounded off to 2) demonstrated that a bar could not be made because the composition was too adhesive/sticky for compression in standard manufacturing equipment. Where production machinery was slowed to an unacceptable level to compress the composition, it was found that its release characteristics were poor because of its tendency to stick to the shaping machinery. Therefore, the advantages of the balance of surfactant activity with mildness was only realistically obtained with an average ethoxy value of 1 when a shaped solid personal cleansing composition is desired. When a free fatty acid is present, the content of sulfonate, free fatty acid and moisture should be carefully managed to obtain an acceptable production rate of shaped solids.

A tight distribution around the average value of 1 ethoxy seems to be important for good performance. Of the sulfonate in the composition, no more than about 25 wt. % of the sulfonate components should have an ethoxy value of four or higher, preferably no higher than about 15 wt. % or 13 wt. % and even more preferably, no higher than about 10 or 11 wt. %. It has been found that the higher ethoxylated materials are detrimental in that lather and the processing of shaped solid compositions are adversely affected.

Finally, the counterion to be employed is preferably sodium, thereby making the sodium salt of the ethoxylated alkyl glyceryl ether sulfonate. The sodium salt makes the processing of the solid personal cleansing composition bar easier in that the composition is generally harder, less tacky, and has less bar slough present in the dish, particularly under high humidity conditions than even the potassium salt. However, counterions other than alkali metals can be employed including ammonium and substituted ammonium cations such as diethanolamine, triethanolamine and the like. If a hard solid bar like composition is desired, an alkaline earth counterion can be employed, for example, magnesium.

It has been noted that in combination with other materials used in mild, shaped solid compositions such as free fatty acids, it is particularly preferred to maintain specific ranges of ethoxylated alkyl glyceryl ether sulfonate, free fatty acids and moisture levels in order to achieve a processable composition in terms of tackiness and release from shaping machinery. By free fatty acid is meant long chain alkyl, preferably normal, carboxylic acid such as lauric, myristic, palmitic and stearic. In general, the higher the sulfonate content, the lower is the free fatty acid and/or moisture content. In general, the higher is the moisture content, the lower the sulfonate and/or the free fatty acid content. In general, the higher the free fatty acid content the lower the sulfonate and/or the moisture content. When a free fatty acid is present in a shaped solid composition such as a bar for personal care use, there is generally about 3 to about 9 wt. %, preferably about 4 to about 8 wt. % of ethoxy alkyl glyceryl ether sulfonate in the composition. There is generally about 2 to about 8 wt. % of free fatty acid in the composition, preferably no more than about 7 wt. %. With respect to the moisture in the composition there is from about 4 to about 13 wt. %, preferably about 5 or 6 to about 10 wt. %. Also present in the composition may be a significant amount of soap, that is long chain alkyl carboxylate salt such as a sodium potassium or ammonium salt. This generally can be from about 8 to about 85 wt. % of the composition, preferably about 45 to about 80 wt. % of the composition. Other anionic surfactants can be present, for example, sulfates, taurates, olefin sulfonates, ethoxylated sulfates, sulfosuccinate, sulfonates, isethionates and the like, generally as their alkali metal or ammonium salts. Generally, these surfactants other than soap may be present in from about 5 to about 55 wt. %, of the composition. It is preferable to maintain low quantities of such additional anionic surfactants in the solid composition such as 5 to about 20 wt. %, or even omit any or all of them entirely, particularly the isethionates. Preferred compositions do not have any isethionates present. It should also be noted that with respect to solid compositions having the desired composition of ethoxy alkyl glyceryl ether sulfonate, moisture and free fatty acid of this paragraph, the alkyl in the ethoxy alkyl glyceryl ether sulfonate is from about 10 to about 20 carbon atoms in length, preferably about 12 to about 18 carbon atoms, more preferably about 12 to about 15 carbon atoms. Preferably less than about 50% of the alkyl groups are branched, that is at least about 50% of the alkyl group or normal, more preferably less than about 30 wt % are branched. Preferably no more than about 25 wt % of the sulfonates have an average ethoxy value of four or more, more preferably no more than about 15 wt % of the sulfonates, still more preferably no more than about 13 wt % or about 11 wt %. The alkyl is preferably 100% alkyl; however, there can be some unsaturation present, particularly because the source of the alkyl group may be a natural product. However, these should preferably be not more than about 20 wt. % of the alkyl groups which have unsaturation, i.e. not more than about 20 wt. % are alkenyl, preferably no more than about 10 wt %. Preferably the average value of ethoxy is about 1.

Other materials can be present in the composition such as preservatives, colorants, antibacterial agents, and the like.

Below are examples of the invention showing the superiority of the inventive compositions. These examples are intended to be illustrative of the invention while not being unduly limiting thereof.

EXAMPLES 1–9

The following compositions were prepared from ethoxylated glyceryl ether sulfonates wherein the counterion is sodium, the alkyl is 14 to 15 carbon atoms, having less than 30 wt. % of the alkyl groups branched and less than about 20 wt. % of the alkyl is alkenyl i.e., unsaturated, the average value of ethoxy group is about 1 and there is less than about 13 wt. % of sulfonate components having ethoxy groups with a value of 4 or more. The free fatty acid (FFA) is a mixture of coco and stearic acid. The moisture is as designated. All quantities are in wt. % of the composition.

Processing trials were made with two soap bases: 60 wt % tallow/40 wt % coco soap and 20 wt % palm/40 wt % palm stearin/40 wt % coco blends. The tallow, coco, palm and palm stearin are the natural sources of the fatty acid salts of the soap.

200 pounds batches of chips having the composition of soap, free fatty acid, sulfonate and moisture as identified below, were processed in a Mazzoni dryer. The batches were then mixed with titanium dioxide (0.5% of final composition) and fragrance in an amalgamator (Model A-2401). The batch time was approximately 3 minutes and the temperature about 25° C. The chips were further refined in a Mazzoni refining plodder (two-stage, single screw, with 30 mesh screens in the initial and final stages). The refined chips were further extruded through the Mazzoni plodder. Typical conditions used in the plodders were: 60–100 F water in the barrels, vacuum in the range of 18–23 inch Hg, average core billet temperature of 95–115 F, billet hardness in the range of 90–98 (measured by Dietert, Green Hardness "B" Scale). The billets were cut to a length of 101 mm using Mazzoni TV-A cutter and pressed in SAS Condor Press (Flash stamping), with pin-dies to give a bar of about 96 grams. The die refrigeration temperature was maintained in the range of −15 to −27 F, preferably closer to the lower limit. A non-interrupted pressing rate of at least 40 strokes/min, preferably closer to 50, sustained for at least 20 minutes was considered acceptable. Results from various experiments are shown below. The remainder of the composition in wt % is almost all soap.

| Example | Soap Base (PO/PS/CO) wt (%) | Fatty Acid wt (%) | Sulfonate wt (%) | $H_2O$ wt (%) | Stroke/ Minute |
|---|---|---|---|---|---|
| 1. | 20/40/40 | 7 | 8 | 4–6 | >50 |
| 2. | 60T/40CO | 7 | 8 | 4–9 | very low |
| 3. | 20/40/40 | 3 | 8 | 39 | 40 |
| 4. | 20/40/40 | 3 | 8 | 8 | 42 |
| 5. | 20/40/40 | 5 | 4 | 6–7.5 | >50 |
| 6. | 20/40/40 | 5 | 6 | 9 | >50 |
| 7. | 20/40/40 | 8 | 6 | 7–8 | 10 |
| 8. | 20/40/40 | 6 | 5 | 8 | >50 |
| 9. | 20/40/40 | 7 | 6 | 6–7 | 40 |

PO/PS/CO - palm/palm stearin/coco soap
T/CO - tallow/coco

A non tallow containing or less than about 20 wt % of the soap in the composition being tallow based is preferred.

We claim:

1. A shaped solid personal cleansing composition comprising
   a. about 80 to about 85 wt. % soap,
   b. about 3 to 7 wt. % of a free fatty acid,
   c. about 4 to about 8 wt. % of an ethoxylated alkyl glyceryl ether sulfonate wherein the average value of ethoxy is about 1 and alkyl is about 12 to about 15 carbon atoms, with no more than 50 wt. % branched alkyl, no more than 20 wt. % alkenyl, and no more than 25 wt. % of the sulfonate component having ethoxy groups with a value of four or more, and
   d. about 4 to 10 wt. % of moisture wherein the value of b, c and d are selected so that a non-interrupted pressing rate of at least 40 strokes/minute sustained for at least 20 minutes is achieved in a SAS Conder presser to give a bar of about 96 grams.

2. The composition in accordance with claim 1 wherein the solid shaped composition is in the form of a bar.

3. The composition in accordance with claim 2 wherein
   a. the soap is present in from about 45 to about 80 wt. % of the composition,
   b. the free fatty acid is about 2 to about 7 wt. % of the composition,
   c. the sulfonate is from about 4 to about 8 wt. % of the composition and the alkyl is from about 12 to about 15 carbon atoms, and
   d. the moisture is from about 5 to about 10 wt. % of the composition.

4. The composition in accordance with claim 3 wherein the processing rate is at least 50 strokes/minute.

* * * * *